US008013130B2

(12) United States Patent
Yanagawa et al.

(10) Patent No.: US 8,013,130 B2
(45) Date of Patent: Sep. 6, 2011

(54) CARBON-BASED SOLID ACID, CATALYST COMPRISING THE SOLID ACID, AND REACTION USING THE SOLID ACID AS CATALYST

(75) Inventors: Shinichirou Yanagawa, Yokohama (JP); Hidesato Kondo, Yokohama (JP); Michikazu Hara, Yokohama (JP)

(73) Assignees: Nippon Oil Corporation, Tokyo (JP); Tokyo Institute of Technology, Tokyo (JP)

( * ) Notice: Subject to any disclaimer, the term of this patent is extended or adjusted under 35 U.S.C. 154(b) by 203 days.

(21) Appl. No.: 12/282,253

(22) PCT Filed: Mar. 8, 2007

(86) PCT No.: PCT/JP2007/055297
§ 371 (c)(1),
(2), (4) Date: Nov. 12, 2008

(87) PCT Pub. No.: WO2007/105802
PCT Pub. Date: Sep. 20, 2007

(65) Prior Publication Data
US 2009/0099345 A1    Apr. 16, 2009

(30) Foreign Application Priority Data
Mar. 10, 2006  (JP) .................................. 2006-066721

(51) Int. Cl.
*C07G 1/00* (2006.01)
*C08H 7/00* (2011.01)
*C08L 97/00* (2006.01)
*C08F 251/00* (2006.01)
*D01F 9/16* (2006.01)

(52) U.S. Cl. ....... 530/500; 527/300; 527/400; 423/447.9
(58) Field of Classification Search .................. 527/300, 527/400; 530/500; 423/447.9
See application file for complete search history.

(56) References Cited

U.S. PATENT DOCUMENTS

| 3,476,740 A | * | 11/1969 | Blackmore et al. ........... 530/500 |
| 3,961,025 A | * | 6/1976 | Harendza-Harinxma . 423/415.1 |
| 4,318,710 A | * | 3/1982 | Pilipski ..................... 423/445 R |
| 5,043,432 A | * | 8/1991 | Dilling .......................... 530/500 |
| 5,049,661 A | * | 9/1991 | Dilling .......................... 530/500 |
| 5,603,867 A | * | 2/1997 | Ohsaki et al. ................. 252/502 |
| 5,843,393 A | * | 12/1998 | Denton, III et al. ....... 423/447.4 |
| 6,589,904 B1 | * | 7/2003 | Iwasaki et al. ................ 502/180 |
| 7,335,790 B2 | * | 2/2008 | Domen et al. .................. 562/89 |
| 2003/0068556 A1 | * | 4/2003 | Xue et al. .................... 429/231.8 |
| 2004/0097369 A1 | * | 5/2004 | Freel et al. ..................... 502/437 |
| 2005/0207962 A1 | * | 9/2005 | Dietz et al. ................ 423/445 R |
| 2007/0142225 A1 | * | 6/2007 | Baker ........................... 502/425 |
| 2008/0045745 A2 | * | 2/2008 | Domen et al. .................. 562/32 |
| 2008/0227996 A1 | * | 9/2008 | Hara et al. ...................... 558/44 |
| 2009/0131709 A1 | * | 5/2009 | Hara ............................. 560/129 |
| 2009/0137850 A1 | * | 5/2009 | Yanagawa et al. ............ 568/899 |

FOREIGN PATENT DOCUMENTS

| JP | 10-218808 A | 8/1998 |
| JP | 2002-104816 A | 4/2002 |
| JP | 2004-238311 A | 8/2004 |
| WO | WO 2005/029508 A1 | 3/2005 |

OTHER PUBLICATIONS

Toda et al. Nature 438(10), 2005, p. 178 and supplemental content.*
Takagaki, Atsushi, et al. (also Junko Nomura, Michikazu Hara, Shigenobu Hayashi, and Kazunari Domen), "Synthesis Condition and Catalysis of Carbon-Based Solid Strong Acid", The 85th Spring Meeting of the Chemical Society of Japan (2005), 2B5-43.
Takagaki, Atsushi et al. (also Junko Nomura, Kazunari Domen, Takashi Tatsumi, Sigenobu Hayashi, and Michikazu Hara), "Synthesis and Characterization of Carbon-Based Solid Strong Acid Having Large Surface Area", The 96th Meeting of the Catalysis Society of Japan (2005), 4E-21.
Toda, Masakazu et al., "Biodiesel made with sugar catalyst," Nature, vol. 438, 10, p. 178, Nov. 2005.
Non-Patent Document 4: Catalyst, vol. 18, No. 6, p. 180-184, 1976.
Non-Patent Document 5: Journal of the Japan Petroleum Institute, vol. 34, No. 3, p. 201-209, 1991.
Hara, Michikazu et al.: "A Carbon Material as a Strong Protonic Acid," Angewandte Chemie, 2004, vol. 43, No. 22, pp. 2955-2958.
International Search Report dated May 29, 2007 (mailed) issued in PCT/JP2007/055297.

* cited by examiner

*Primary Examiner* — Mark Eashoo
*Assistant Examiner* — Liam Heincer
(74) *Attorney, Agent, or Firm* — Weingarten, Schurgin, Gagnebin & Lebovici LLP

(57) ABSTRACT

A carbon-based solid acid which has high activity and high thermal stability and is useful as an acid catalyst for various reactions such as hydration of olefins.
The carbon-based solid acid for use as a catalyst is obtained by carbonization and sulfonation of an organic substance, which has a reduction rate of 10 mol % or less of acid content as measured by immersing the solid acid in hot water at 120° C. for 2 hours, is used as the acid catalyst.
The organic substance to be used as the raw material for preparing the solid acid is preferably a saccharide having β1-4 glycosidic bond (e.g. cellulose) or lignin. Amylose is also suitable as the raw material. Examples of the reaction for which the solid catalyst can be used include hydration of olefins, etherification of olefins, and acid/alcohol esterification.

5 Claims, No Drawings

CARBON-BASED SOLID ACID, CATALYST COMPRISING THE SOLID ACID, AND REACTION USING THE SOLID ACID AS CATALYST

This application is a §371 national phase filing of PCT/JP2007/055297 filed Mar. 8, 2007, and claims priority to Japanese Appln No. 2006-066721 filed Mar. 10, 2006.

FIELD OF THE INVENTION

The present invention relates to a sulfonic acid group-containing carbonaceous material produced by carbonization and sulfonation of an organic substance (hereinafter referred to as "carbon-based solid acid"), a catalyst comprising the solid acid, and methods for various reactions such as hydration of olefins using the solid acid as catalyst.

BACKGROUND OF THE INVENTION

Solid acids are useful for various purposes and, particularly, promising in use as catalyst for various reactions in an industrial process because the process can be simplified, and various types of solid acids have been developed therefore. A typical one of such solid acids is ion-exchange resin which is a polymer having sulfonic acid group. However, the ion-exchange resin has limited uses or using conditions due to defects such as low thermal stability. Nafion or the like that is a high heat-resistance resin has been also developed, but it is too expensive to be used for industrial purposes. In such a situation, carbon-based solid acids which can be obtained by carbonization and sulfonation of an aromatic compound or saccharide have been developed. Such carbon-based solid acids are recently attracting attentions due to inexpensiveness in addition to high performance (high activity), and being tried, as applications thereof, to be used as a proton conductive material or a catalyst for esterification reaction or the like (refer to Non-Patent Document 1, Non-Patent Document 2, Non-Patent Document 3, Patent Document 1, and Patent Document 2).

On the other hand, the solid acids are useful also as catalyst for hydration of olefins. The hydration reaction of olefins is a reaction important for production of alcohols, ketones or the like, and industrially utilized. Isopropyl alcohol, 2-butanol, and methyl ethyl ketone are produced by various methods using hydration of propylene or n-butene (Non-Patent Document 4 and Non-Patent Document 5). At present, a method using sulfuric acid (indirect hydration method) is mainly adapted in plants in the world. However, this method involves many by-products and needs a large quantity of sulfuric acid, causing problems such as sulfuric acid corrosion of an apparatus, reuse treatment of sulfuric acid and liquid waste disposal. Therefore, a direct hydration method or the like using solid acid as catalyst is also being developed, including, for example, a method using, as catalyst, an ion-exchange resin or a solid acid in which a mineral acid such as phosphoric acid is supported by a carrier. However, in these cases, decrease in activity or corrosion of apparatus may be caused by elimination of ion-exchange group (sulfonic acid group) by hydrolysis or desorption of the supported acid from the carrier during reaction, and measures thereto must be taken. Further, the ion-exchange resin-based catalyst has problems such as expensiveness of the catalyst, restriction of reaction temperature from the point of the heat resistance of the resin, and the like.

In the above-mentioned recently-developed carbon-based solid acids, it is considered that various organic substances are usable as the raw material therefor, and examples using condensed aromatics such as naphthalene or coronene, heavy oil or pitch containing the condensed aromatic compound, glucose, starch and the like are disclosed. However, there still exist many unclear points, and it cannot be said that a production method for those having performances of industrially practical level is established. With respect to the hydration reaction of olefins, only an example in which hydration reaction of 2,3-dimethyl-2-butene is carried out at low temperature (70° C.) using such a carbon-based solid acid as catalyst is disclosed without concrete disclosure or suggestion of a catalyst, a reaction condition and the like which are industrially practicable in application to other olefins (Non-Patent Document 6).

In any case, the solid acids mentioned above are recognized to have a problem in the resistance of the acid radical possessed thereby.

Non-Patent Document 1: "Synthesis Condition and Catalysis of Carbon-Based Solid Strong Acid" Atsushi Takagaki, Junko Nomura, Michikazu Hara, Shigenobu Hayashi, and Kazunari Domen, The 85$^{th}$ Spring Meeting of the Chemical Society of Japan (2005), 2B5-43

Non-Patent Document 2: "Synthesis and Characterization of Carbon-Based Solid Strong Acid Having Large Surface Area" Atsushi Takagaki, Junko Nomura, Kazunari Domen, Takashi Tatsumi, Sigenobu Hayashi, and Michikazu Hara, The 96$^{th}$ Meeting of the Catalysis Society of Japan (2005), 4E-21

Non-Patent Document 3: Nature, 438, 10, p. 178, November, 2005

Non-Patent Document 4: Catalyst, Vol. 18, No. 6, p. 180-184, 1976

Non-Patent Document 5: Journal of the Japan Petroleum Institute, Vol. 34, No. 3, p. 201-209, 1991

Non-Patent Document 6: Angew. Chem. Int. Ed., 43, 2955-2958 (2004)

Patent Document 1; Japanese Patent Application Laid-Open No. 2004-238311

Patent Document 2: WO 2005/029508

SUMMARY OF THE INVENTION

The present invention has an object to provide a carbon-based solid acid which has high activity and high thermal stability and is useful as catalyst for various reactions such as hydration of olefins.

A first aspect of the invention relates to a carbon-based solid acid obtained by carbonization and sulfonation of an organic substance, and having a reduction rate of 10 mol % or less of acid content caused by immersing the solid acid in hot water of 120° C. for 2 hours.

A second aspect of the invention relates to a carbon-based solid acid wherein the organic substance in the first aspect of the invention comprises a saccharide having β1-4 glycoside bond.

A third aspect of the invention relates to a carbon-based solid acid wherein the organic substance in the first aspect of the invention comprises cellulose or lignin.

A fourth aspect of the invention relates to a carbon-based solid acid wherein the organic substance in the first aspect of the invention comprises amylose as a main component.

A fifth aspect of the invention relates to a method for producing an olefin hydration product, comprising performing hydration reaction of olefin in the presence of the carbon-based solid acid according to any one of the first to fourth aspects of the invention.

A sixth aspect of the invention relates to a method for producing an ether, comprising performing etherification reaction of olefin in the presence of the carbon-based solid acid according to any one of the first to fourth aspects of the invention.

A seventh aspect of the invention relates to a method for producing an ester, comprising performing esterification reaction by reacting acid with alcohol in the presence of the carbon-based solid acid according to any one of the first to fourth aspects of the invention.

An eighth aspect of the invention relates to a catalyst comprising a carbon-based solid acid obtained by carbonization and sulfonation of an organic substance, which has a reduction rate of 10 mol % or less of acid content caused by immersing the solid acid in hot water of 120° C. for 2 hours.

Since the carbon-based solid acid according to the present invention has high thermal and chemical stabilities and hardly causes elimination of acid by hydrolysis or the like even at high temperature, high durability (long life) can be expected in various uses. The carbon-based solid acid of the present invention can be industrially supplied in large amounts since it can be inexpensively produced. Further, this carbon-based solid acid shows high reaction activity, when used as a catalyst in various polar reactions such as hydration and etherification of olefins, neutralization and purification step after reaction is not necessary, the catalyst can be easily separated and reused, and an intended product can be produced efficiently at low cost without the problem of corrosion of apparatus.

Namely, the solid acid obtained by carbonization and sulfonation of an organic substance, which has a reduction rate of 10 mol % or less of acid content caused by immersing the solid acid in hot water of 120° C. for 2 hours, has not been obtained in the past, and is novel as solid acid.

DETAILED DESCRIPTION OF THE INVENTION

Now the present invention will be described further in detail.

The carbon-based solid acid of the present invention can be obtained by carbonizing and sulfonating an organic substance, particularly, a carbohydrate. As the organic substance, saccharides having β1-4 glycosidic bond, specifically, polysaccharides such as cellobiose and cellulose by condensation of glucose, lignin, and amylose by condensation of glucose as saccharides having α1-4 glycosidic bond are preferably used. Particularly preferred are a polysaccharide having β1-4 glycosidic bond, specifically, cellulose; lignin; and a polysaccharide having α1-4 glycosidic bond, specifically amylose. Such organic substances are preferred to have a molecular weight of 1000 or more from the viewpoint of preparation of the carbon-based solid acid, since sulfuric acid is hardly diluted due to minimized generation of moisture in the carbonization and sulfonation, and the acid content is thus improved. These saccharides can be used independently or in combination of two or more kinds thereof, and further can be used in combination with other organic substances within the limit of not impairing the effect of the invention. In such a case, it is preferred that the above-mentioned saccharides are principally contained (50% or more).

Preferably, by using the above-mentioned specific saccharides, high thermal stability can be ensured. Specifically, a carbon-based solid acid having a reduction rate of 10 mol % or less of acid content caused by immersing the solid acid in hot water of 120° C. for 2 hours can be obtained.

When a polycyclic aromatic hydrocarbon such as naphthalene, anthracene, perylene or coronene, those containing such aromatic hydrocarbon, for example, pitch or tar, or a monosaccharide, particularly, glucose or the like, is used as the organic substance, the thermal stability of the resulting carbon-based solid acid is deteriorated, with the reduction rate of acid content exceeding 10 mol %.

The carbonization of the organic substance mentioned above is attained by performing heat treatment under an inert gas atmosphere of nitrogen or the like, and an amorphous black solid (carbonized material) is obtained thereby. The sulfonation is attained by performing heat treatment in concentrated sulfuric acid or fuming sulfuric acid, whereby sulfonic acid group is added to the skeleton of the carbonized material. The sulfonation is preferably performed after completion of the carbonization, but may be performed simultaneously with the carbonization. The conditions for the carbonization and the sulfonation are properly selected depending on the kind of the organic substance to be used. The carbonization is preferably performed in nitrogen atmosphere at 250 to 600° C. for 1 to 50 hours, and the sulfonation is preferably performed at 100 to 450° C. for 0.5 to 30 hours. The degree of carbonization is determined based on the degree of graphitization, and the peak intensity ratio D/G of D-peak to G-peak in Raman spectroscopy that is one of indexes (parameters) showing the degree of graphitization is 0.5 or more. The graphitization is not performed to 100%.

The heating temperature in simultaneous treatment of carbonization and sulfonation is preferably 100 to 300° C., further preferably 150 to 270° C. After completion of the carbonization and sulfonation, removal of excessive sulfuric acid is performed by washing with hot water, and drying is further performed, whereby the carbon-based solid acid of the invention can be obtained. The washing with hot water can be easily performed, for example, under reflux at about 100° C. by means of Soxhlet extraction or the like. The washing time can be also shortened by performing the washing at high temperature under pressure. The washing with hot water is performed until sulfuric acid in washing water becomes substantially undetectable. The carbon-based solid acid of the invention is substantially amorphous such that any structure cannot be confirmed from an X-ray diffraction pattern.

The thus-obtained carbon-based solid acid of the invention has high thermal stability with the reduction rate of acid content being as small as 10 mol % or less in a hot water heat resistance evaluation test performed by immersing the solid acid in hot water of 120° C. for 2 hours. The measurement of reduction in acid content is performed to the carbon-based solid acid before and after the hot water treatment by conventionally known neutralization titration method, back titration method or the like. The carbon-based solid acid of the present invention can be industrially used as catalyst advantageously in various reactions, for example, in polar reaction, since the reduction rate of acid content during the reactions is low.

The carbon-based solid acid of the invention has such acid strength and acid content as to be useful for acid catalysis as solid acid catalyst. This solid acid is advantageously used, preferably, as catalyst for various polar reactions such as esterification reaction of alcohol with acid, and hydration reaction and etherification reaction of olefins, although it can function as an acid catalyst even under a hydrophobic condition. Namely, this solid acid is useful as catalyst for a polar reaction using a polar substance such as alcohol, carboxylic acid or water as a reactive substrate, since it exhibits excellent durability in such a polar reaction.

Olefin hydration (reaction of olefins with water), olefin etherification (reaction of olefins with alcohol), and olefin esterification (reaction of carboxylic acid with alcohol), in which the carbon-based solid acid of the present invention is used as acid catalyst, will be then described.

There is no particular limit on the olefins used in the present invention, and straight, branched and cyclic ones can be used. However, olefins having a carbon number of 2 to 5, specifically, propylene, and butenes such as 1-butene, 2-butene and isobutene are preferably used. Although the water to be used in the hydration is not particularly limited, it is preferred to use ion-exchange water or distilled water (including vapor condensate).

The alcohols used for the etherification reaction are not particularly limited. However, alcohols having a carbon number of 1 to 4, specifically, methanol, ethanol, and isopropyl alcohol are preferably used. The molar ratio of water or alcohol to olefin is set generally to 0.1 to 10, preferably to 0.3 to 7, further preferably to 1 to 5 although it is not particularly limited. If the amount of water or alcohol is too small, a side reaction such as dimerization of olefin is caused, and if it is too large, the productivity is undesirably deteriorated.

As the alcohol used for the esterification reaction, the same alcohols as those described above can be used. Examples of the carboxylic acid used for the esterification include saturated or unsaturated carboxylic acids having a carbon number of 1 to 4, specifically, acetic acid, acrylic acid, and methacrylic acid. The molar ratio of the alcohol to the acid is set generally to 0.1 to 100 although it is not particularly limited thereto. The acid to be used may be anhydride.

The reaction temperature in the hydration reaction and etherification reaction of olefins is set generally to 60° C. or higher for promoting the reaction, and preferably to 100° C. or higher, further preferably to 120° C. or higher for ensuring high activity. The reaction temperature is set preferably to 250° C. or lower, since an excessively high temperature may cause decomposition of the catalyst. The reaction pressure is set generally to 1 MPa or more, for promoting the reaction, preferably to 3 MPa or more, further preferably to 5 MPa or more although it is not particularly limited thereto. The reaction pressure is set preferably to 20 MPa or less since an excessively high pressure may lead to increase in facility cost. It can be properly selected depending on the reaction form. As the reaction form, any one of gas phase, liquid phase and gas-liquid mixed phase can be adapted. When reactive distillation is performed at ordinary pressure, a temperature of 100° C. or lower is usually adapted. Specifically, the etherification reaction is usually performed at 80 to 100° C., and the hydration reaction (isobutene) is performed at 60 to 100° C.

The same condition can be adapted also in the esterification. The reaction can be easily promoted by appropriately removing water generated in accordance with the progress of the reaction from the reaction system.

In the hydration reaction, a solvent can be used together. As the solvent, an amphipathic solvent is preferred for preventing separation of the reaction solution to water phase and oil phase. For example, ethers, glycol ethers, alcohols, ketones and the like can be used. Although the solvent is usable similarly in the etherification reaction, the solvent is not needed unless phase separation occurs.

The hydration reaction of olefins in the present invention is simpler in process than an indirect hydration method using sulfuric acid catalyst (two-stage reaction of sulfuric acid esterification and hydrolysis) since it is a direct hydration method (single stage reaction). Further, the indirect hydration method needs a neutralization and purification step for removal of sulfuric acid, a concentration step for reuse of sulfuric acid and like steps, which complicate the process. However, in the method of the present invention, the catalyst can be easily separated for reuse by filtration, centrifugal separation or the like since the catalyst is solid, and the neutralization and purification step as in the indirect hydration method is not needed since the reaction solution after removing the catalyst contains no acid catalyst component. Reaction products can be appropriately purified by distillation or the like after the catalyst removal. Reactive distillation can be also performed. In the etherification reaction of olefins in the present invention, reactive distillation or a method by fixed bed is generally adapted.

In each of the hydration, the etherification and the esterification reactions, operation at high temperature can be performed by using the catalyst of the present invention, and reaction activity is consequently increased. Therefore, miniaturization of a reactor can be attained. The replacement frequency of catalyst can be also reduced since the catalyst exhibits high thermal stability.

The present invention will be further concretely described by examples shown below. However, the present invention is never limited by these examples.

Example 1

Carbon-Based Solid Acid Obtained from Cellulose

Preparation of Solid Acid 40.0 g of cellulose was heat-treated at 400° C. for 5 hours under nitrogen atmosphere to thereby obtain 10.8 g of carbonized material. Sulfonation was performed by adding, to 3.0 g of this carbonized material, 150 g of concentrated sulfuric acid followed by heat treatment at 150° C. for 15 hours under nitrogen atmosphere. After completion of the sulfonation, a black solid matter was filtered by a glass filter and repeatedly washed with hot water under reflux (about 100° C.), and neutralization titration was performed to confirm that no sulfuric acid was detected in the washing water. Finally, drying was performed to thereby obtain 3.0 g of a black powdery (amorphous) carbon-based solid acid A. The acid content of the solid acid measured by back titration was 3.51 mmol/g.

Analysis of Catalyst

The carbon-based solid acid A was subjected to X-ray analysis. In the X-ray analysis, an X-ray refraction device (MXP 18VAHF) by Mac Science Co., Ltd. was used for measurement. As a result, no peak which could specify the structure was detected from the analysis pattern of this solid acid, and this solid acid was found to be an amorphous substance. The carbon-based solid acid A was then subjected to elemental analysis. In the elementary analysis, elementar vario EL was used for measurement. As a result, it was found that sulfonic acid group was introduced to this solid acid with inclusion of sulfur in a C/S ratio of 74.7.

The carbon-based solid acid A was subjected to 13C-DDMAS nuclear magnetic resonance spectral analysis. In this analysis, NMR Systems 400WB by Varian Inc. was used for measurement. As a result, it was confirmed that the carbons of the solid acid were mostly derived from aromatic group.

The degree of graphitization of the carbon-based solid acid A was measured. Raman spectroscopic analysis was used for the measurement.

In this analysis, a laser Raman spectroscopic analyzer HOLOLAB 5000R was used. The peak intensity ratio of G-peak which appears near 1580 cm−1 and D-peak which appears near 1400 cm−1 was calculated, and the calculated peak intensity ratio D/G was taken as the degree of graphitization. As a result, the degree of graphitization was 0.63. Each solid acid having high reaction activity in various reactions was confirmed to have a degree of graphitization of 0.5 to 0.7.

Hot Water Heat Resistance Evaluation Test

To 20.0 g of water put in a 50-cc stainless steel sealed vessel, 0.20 g of the carbon-based solid acid A was added followed by sealing, heated to a temperature of 120° C., and retained at that temperature for 2 hours. After completion of heating, the reaction mixture was cooled, and the solid acid was then taken out therefrom and subjected to acid content measurement. The degree of acid reduction was measured by comparing the measured acid content with the acid content before testing. As a result, the acid content after testing was 3.36 mmol/g, with the reduction rate of acid content being 4 mol %. The reduction rates of acid content after testing as measured by changing the evaluation test temperature to 150, 180 and 210° C. were 5 mol %, 8 mol %, and 11 mol %, respectively.

Hydration Reaction

To a 200-cc autoclave with stirrer, water and dioxane (solvent) were put in predetermined amounts, respectively, 0.20 g of the carbon-based solid acid A was added thereto followed by sealing, and a predetermined amount of propylene, 1-butene or isobutene was injected and sealed therein. The reaction mixture was heated to a predetermined temperature while stirring at 700 rpm, pressure-adjusted with nitrogen as needed, maintained at the predetermined temperature to thereby perform hydration reaction for 2 hours. After completion of the reaction, the reaction solution was cooled, and then subjected to quantitative analysis by TCD-GC. The acid content of the catalyst was measured by back titration, and compared with the acid content before the reaction to measure the reduction rate of the acid content. The reaction conditions and reaction results are summarized in Table 1-1.

TABLE 1-1

| Olefin | Amount of olefin | Amount of solvent (g) | Amount of water | Water/Olefin (molar ratio) | Pressure (MPa) | Temperature (° C.) | Amount of produced alcohol (mmol/cat-g/h) | Acid content after reaction (mmol/g) | Reduction rate of acid content (mol %) |
|---|---|---|---|---|---|---|---|---|---|
| Propylene | 10.5 g (0.25 mol) | 15.0 | 9.0 g (0.5 mol) | 2 | 5.0 | 120 | Isopropyl alcohol 0.52 | 3.35 | 4% |
| 1-Butene | 14..3 g (0.25 mol) | 15.0 | 9.0 g (0.5 mol) | 2 | 5.0 | 150 | s-Butyl alcohol 1.50 | 3.16 | 10% |
| Isobutene | 8.4 g (0.15 mol) | 9.0 | 5.4 g (0.3 mol) | 2 | 1.3 | 110 | t-Butyl alcohol 193 | 3.19 | 9% |

Etherification Reaction

Each of various alcohols was put in a 200-cc autoclave with stirrer in a predetermined amount, 0.20 g of the carbon-based solid acid A was added thereto followed by sealing, and each of various olefins was injected and sealed therein in a predetermined amount. The reaction mixture was heated to a predetermined temperature while stirring at 700 rpm, pressure-adjusted with nitrogen as needed, and then retained at the predetermined temperature to thereby perform etherification reaction for 2 hours. After completion of the reaction, the reaction mixture was cooled and then subjected to quantitative analysis by TCD-GC. The measurement of acid content of the catalyst was performed by back titration, and the measured acid content was compared with the acid content before the reaction to measure the reduction rate of the acid content. The reaction conditions and reaction results are shown in Table 1-2.

TABLE 1-2

| Olefin | Amount of olefin | Alcohol | Amount of Alcohol | Alcohol/Olefin (molar ratio) | Pressure (MPa) | Temperature (°C.) | Amount of produced ether (mmol/cat-g/h) | Acid content after reaction (mmol/g) | Reduction rate of acid content (mol %) |
|---|---|---|---|---|---|---|---|---|---|
| Propylene | 21 g (0.5 mol) | Isopropyl alcohol | 15.0 g (0.25 mol) | 0.5 | 5.0 | 110 | Diisopropyl ether 0.40 | 2.49 | 29% |
| Isobutene | 28.1 g (0.5 mol) | Ethanol | 11.5 g (0.25 mol) | 0.5 | 1.7 | 110 | Ethyl t-butyl ether 878 | 2.18 | 38% |

Esterification Reaction 30-cc of various alcohols was put in a 100-cc eggplant-shaped flask, each of various carboxylic acids was added so as to have a molar ratio of 1/50 to the alcohol, and 0.20 g of the carbon-based solid acid A was added thereto followed by heating. The reaction mixture was stirred and reacted for 2 hours at a reflux temperature, and then rapidly cooled in a water bath to stop the reaction. After completion of the reaction, a quantitative analysis was performed by TCD-GC. The acid content of the catalyst was measured by back titration, and the measured acid content was compared with the acid content before the reaction to measure the reduction rate of the acid content. The reaction conditions and reaction results are shown in Table 1-3.

the heat treatment, and 3 g of the carbonized material was sulfonated to thereby obtain 3.20 g of a carbon-based solid acid B. The acid content of the solid acid measured by back titration was 3.57 mmol/g.

Hot Water Heat Resistance Evaluation Test

Hot water heat resistance evaluation test was performed to the carbon-based solid acid B by the same method as in Example 1. As a result, the acid content after testing was 3.51 mmol/g, with the reduction rate of acid content being 2 mol %.

TABLE 1-3

| Carboxylic acid | Amount of carboxylic acid | Alcohol | Amount of Alcohol | Amount of produced ester (mmol/cat-g/h) | Acid content after reaction (mmol/g) | Reduction rate of acid content (mol %) |
|---|---|---|---|---|---|---|
| Acrylic acid | 1.07 g (0.015 mol) | Methanol | 23.73 g (0.74 mol) | Methyl acrylate 3.0 | 2.97 | 16% |
| Acetic acid | 0.63 g (0.011 mol) | Ethanol | 23.69 g (0.514 mol) | Ethyl acetate 14.1 | 3.14 | 10% |

Example 2
Carbon-Based Solid Acid Obtained from Lignin

Preparation of Solid Acid

A solid acid was prepared according to Example 1, except that lignin was used as the raw material instead of cellulose. As a result, 24.8 g of carbonized material was recovered after Hydration Reaction The carbon-based solid acid B was subjected to hydration reaction by the same method as in Example 1. The reaction condition and reaction result are summarized in Table 2.

TABLE 2

| Olefin | Amount of olefin | Amount of solvent (g) | Amount of water | Water/Olefin (molar ratio) | Pressure (MPa) | Temperature (°C.) | Amount of produced alcohol (mmol/cat-g/h) | Acid content after reaction (mmol/g) | Reduction rate of acid content (mol %) |
|---|---|---|---|---|---|---|---|---|---|
| Propylene | 10.5 g (0.25 mol) | 15.0 | 9.0 g (0.5 mol) | 2 | 5.0 | 120 | Isopropyl alcohol 0.17 | 3.15 | 12% |

Example 3

Carbon-Based Solid Acid Obtained from Amylose

Preparation of Solid Acid

A solid acid was prepared according to Example 1, except that amylose was used as the raw material instead of cellulose. As a result, 18 g of carbonized material was recovered after the heat treatment, and 3 g of the carbonized material was sulfonated to thereby obtain 1.20 g of a carbon-based solid acid C. The acid content of the solid acid measured by back titration was 3.33 mmol/g.

Hot Water Heat Resistance Evaluation Test

Hot water heat resistance evaluation test was performed to the carbon-based solid acid C by the same method as in Example 1. As a result, the acid content after testing was 3.28 mmol/g, with the reduction rate of acid content being 2 mol %.

Hydration Reaction

The carbon-based solid acid C was subjected to hydration reaction by the same method as in Example 1. The reaction condition and reaction result are summarized in Table 3.

sulfonated to thereby obtain 3.12 g of a carbon-based solid acid E. The acid content of the solid acid measured by back titration was 3.05 mmol/g.

Hot Water Heat Resistance Evaluation Test

Hot water heat resistance evaluation test was performed to the carbon-based solid acid E by the same method as in Example 1. As a result, the acid content after testing was 2.41 mmol/g, with the reduction rate of acid content being 21 mol %. The reduction rates of acid content after testing as measured by changing the evaluation test temperature to 180° C. and 210° C. were 28 mol % and 33 mol %, respectively, which are apparently inferior in heat resistance to those of the solid acids of Examples of present invention.

TABLE 3

| Olefin | Amount of olefin | Amount of solvent (g) | Amount of water | Water/Olefin (molar ratio) | Pressure (MPa) | Temperature (° C.) | Amount of produced alcohol (mmol/cat-g/h) | Acid content after reaction (mmol/g) | Reduction rate of acid content (mol %) |
|---|---|---|---|---|---|---|---|---|---|
| Propylene | 10.5 g (0.25 mol) | 15.0 | 9.0 g (0.5 mol) | 2 | 5.0 | 120 | Isopropyl alcohol 0.08 | 3.05 | 5% |

Comparative Example 1

Carbon-Based Solid Acid Obtained from Glucose

Preparation of Solid Acid

A solid acid was prepared according to Example 1, except that glucose was used as the raw material instead of cellulose. As a result, 11.7 g of carbonized material was recovered after the heat treatment, and 3 g of the carbonized material was Hydration Reaction The carbon-based solid acid E was subjected to hydration reaction by the same method as in Example 1. The reaction conditions and reaction results are summarized in Table 4-1. The reduction rate of acid content in each reaction is large, compared with those of Examples, which shows that the heat resistance is low.

TABLE 4-1

| Olefin | Amount of olefin | Amount of solvent (g) | Amount of water | Water/Olefin (molar ratio) | Pressure (MPa) | Temperature (° C.) | Amount of produced alcohol (mmol/cat-g/h) | Acid content after reaction (mmol/g) | Reduction rate of acid content (mol %) |
|---|---|---|---|---|---|---|---|---|---|
| Propylene | 10.5 g (0.25 mol) | 15.0 | 9.0 g (0.5 mol) | 2 | 5.0 | 120 | Isopropyl alcohol 0.34 | 2.31 | 21% |
| 1-Butene | 14..3 g (0.25 mol) | 15.0 | 9.0 g (0.5 mol) | 2 | 5.0 | 150 | s-Butyl alcohol 1.52 | 1.84 | 40% |
| Isobutene | 8.4 g (0.15 mol) | 9.0 | 5.4 g (0.3 mol) | 2 | 1.3 | 110 | t-Butyl alcohol 122 | 1.88 | 38% |

Etherification Reaction

The carbon-based solid acid E was subjected to etherification reaction by the same method as in Example 1. The reaction conditions and reaction results are shown in Table 4-2. The reduction rate of acid content in each reaction is large, compared with those of Examples, which shows that the heat resistance is low.

TABLE 4-2

| Olefin | Amount of olefin | Alcohol | Amount of Alcohol | Alcohol/Olefin (molar ratio) | Pressure (MPa) | Temperature (° C.) | Amount of produced ether (mmol/cat-g/h) | Acid content after reaction (mmol/g) | Reduction rate of acid content (mol %) |
|---|---|---|---|---|---|---|---|---|---|
| Propylene | 21 g (0.5 mol) | Isopropyl alcohol | 15.0 g (0.25 mol) | 0.5 | 5.0 | 110 | Diisopropyl ether 1.6 | 1.27 | 58% |
| Isobutene | 28.1 g (0.5 mol) | Ethanol | 11.5 g (0.25 mol) | 0.5 | 1.7 | 110 | Ethyl t-butyl ether 517 | 0.94 | 69% |

Comparative Example 2

Amberlyst 15E

Hot Water Heat Resistance Evaluation Test

Commercially available Amberlyst 15E was subjected to hot water heat resistance evaluation test by the same method as in Example 1. As a result, the acid content before testing was 4.85 mmol/g, while the acid content after testing was 4.07 mmol/g, with the reduction rate of acid content being 16 mol %. When the evaluation test temperature was changed to 210° C., the reduction rate of acid content after evaluation was 69 mol %, which shows that the heat resistance is significantly inferior to that of the solid acid of the present invention.

Hydration Reaction

Commercially available Amberlyst 15E was subjected to hydration reaction by the same method as in Example 1. The reaction condition and reaction result are shown in Table 5. The table shows that Amberlyst is highly active, but larger in acid reduction than those of Examples, and thus inappropriate for industrial long-term operations.

Comparative Example 3

Carbon-Based Solid Acid Prepared from Heavy Oil

Preparation of Solid Acid

To 20 cc of Heavy oil A (Defined by Japanese Industrial Standards), 40 cc of fuming sulfuric acid was added followed by heat treatment at 100° C. for 1 hour under nitrogen atmosphere. After completion of heating, a resulting black solid matter was filtered by a glass filter and repeatedly washed with hot water under reflux (at about 100° C.) until it was confirmed that no sulfuric acid was detected in the washing water. Finally, drying was performed to thereby obtain 3.1 g of a black powdery (amorphous) carbon-based solid acid F. The acid content of the solid acid measured by back titration was 3.41 mmol/g.

Hot Water Heat Resistance Evaluation Test

The carbon-based solid acid F was subjected to hot water heat resistance evaluation test by the same method as in Example 1. As a result, the acid content after testing was 2.71 mmol/g, with the reduction rate of acid content being 20 mol %, which is significantly inferior in heat resistance to those of the solid acids of Examples of present invention.

Hydration Reaction

The carbon-based solid acid F was subjected to hydration reaction by the same method as in Example 1. The reaction condition and reaction result are shown in Table 6. The reduction amount of acid content in this reaction is large, compared with those in Examples, which shows that the heat resistance is low.

TABLE 5

| Olefin | Amount of olefin | Amount of solvent (g) | Amount of water | Water/Olefin (molar ratio) | Pressure (MPa) | Temperature (° C.) | Amount of produced alcohol (mmol/cat-g/h) | Acid content after reaction (mmol/g) | Reduction rate of acid content (mol %) |
|---|---|---|---|---|---|---|---|---|---|
| Propylene | 10.5 g (0.25 mol) | 15.0 | 9.0 g (0.5 mol) | 2 | 5.0 | 120 | Isopropyl alcohol 4..92 | 4..08 | 16% |

TABLE 6

| Olefin | Amount of olefin | Amount of solvent (g) | Amount of water | Water/Olefin (molar ratio) | Pressure (MPa) | Temperature (°C.) | Amount of produced alcohol (mmol/cat-g/h) | Acid content after reaction (mmol/g) | Reduction rate of acid content (mol %) |
|---|---|---|---|---|---|---|---|---|---|
| Propylene | 10.5 g (0.25 mol) | 15.0 | 9.0 g (0.5 mol) | 2 | 5.0 | 120 | Isopropyl alcohol 0.57 | 2.47 | 27% |

As is apparent from the above-mentioned Examples and Comparative Examples, the solid acid of the present invention has high thermal stability and a low reduction rate of acid content even under high temperature in actual reactions, and is suitable for industrial long-term operations.

INDUSTRIAL APPLICABILITY

The solid acid of the present invention is suitable for industrial long-term operations due to the high thermal stability and minimized reduction in acid content under high temperature.

Therefore, this solid acid can be used as acid catalyst for reactions such as hydration of olefins, etherification of olefins, and esterification by reaction of acid with alcohol.

The invention claimed is:

1. A carbon-based solid acid obtained by carbonization of an organic substance and by sulfonation after completion of carbonization, and having a reduction rate of 10 mol % or less of acid content caused by immersing the solid acid in hot water of 120° C. for 2 hours, wherein the carbonization is performed in inert gas atmosphere at 250 to 600° C. for 1 to 50 hours and the sulfonation is performed at 100 to 450° C. for 0.5 to 30 hours, the peak intensity ratio D/G of D-peak to G-peak for the carbon-based solid acid in Raman spectroscopy is 0.5 or more and less than 1.0; and wherein the organic substance comprises lignin as a main component.

2. An acid catalyst, comprising the carbon-based solid acid according to claim 1.

3. A method for producing an olefin hydration product, comprising performing hydration reaction of an olefin in the presence of the carbon-based solid acid according to claim 1.

4. A method for producing an ether, comprising performing etherification reaction of an olefin in the presence of the carbon-based solid acid according to claim 1.

5. A method for producing an ester, comprising performing esterification by reacting an acid with an alcohol in the presence of the carbon-based solid acid according to claim 1.

* * * * *